United States Patent
Siripalli et al.

(10) Patent No.: US 9,518,028 B2
(45) Date of Patent: Dec. 13, 2016

(54) PROCESS FOR THE PREPARATION OF ROSUVASTATIN CALCIUM AND PREPARATION OF ITS NOVEL INTERMEDIATES

(71) Applicant: SUVEN LIFE SCIENCES LIMITED, Hyderabad, Andhra Pradesh (IN)

(72) Inventors: Udaya Bhaskara Rao Siripalli, Hyderabad (IN); Veera Reddy Arava, Hyderabad (IN); Rajendiran Chinnapillai, Hyderabad (IN); Anji Reddy Middekadi, Hyderabad (IN); Naresh Raju Makaraju, Hyderabad (IN); Venkateswarlu Jasti, Hyderabad (IN)

(73) Assignee: SUVEN LIFE SCIENCES LIMITED, Hyderabad (IN)

( * ) Notice: Subject to any disclaimer, the term of this patent is extended or adjusted under 35 U.S.C. 154(b) by 0 days.

(21) Appl. No.: 14/901,721

(22) PCT Filed: Nov. 18, 2013

(86) PCT No.: PCT/IN2013/000702
§ 371 (c)(1),
(2) Date: Dec. 28, 2015

(87) PCT Pub. No.: WO2015/008294
PCT Pub. Date: Jan. 22, 2015

(65) Prior Publication Data
US 2016/0304468 A1    Oct. 20, 2016

(30) Foreign Application Priority Data
Jul. 16, 2013  (IN) .......................... 3174/CHE/2013

(51) Int. Cl.
C07D 239/42  (2006.01)
C07F 7/18  (2006.01)

(52) U.S. Cl.
CPC .............. *C07D 239/42* (2013.01); *C07F 7/188* (2013.01)

(58) Field of Classification Search
CPC .................................................. C07D 239/42
See application file for complete search history.

(56) References Cited

U.S. PATENT DOCUMENTS

| 4,611,067 A | 9/1986 | Volante |
| RE37,314 E | 8/2001 | Hirai |
| 2006/0089501 A1 | 4/2006 | Niddam-Hildesheim |
| 2007/0167625 A1 | 7/2007 | Balanov |

(Continued)

FOREIGN PATENT DOCUMENTS

| CN | 102181493 | 9/2011 |
| CN | 102181493 B | * 6/2015 |

(Continued)

OTHER PUBLICATIONS

CAS Abstract of CN 102181493, Accession No. 155:455571 (2011).*

(Continued)

*Primary Examiner* — Alexander R Pagano
(74) *Attorney, Agent, or Firm* — Iphorgan Ltd.

(57) ABSTRACT

The present invention relates to process for the preparation of 7-[4-(4-fluorophenyl)-6-isopropyl-2-(N-methyl-N-methylsulfonylamino)pyrimidin-5-yl]-(3R,5S)-dihydroxy-(E)-6-heptenoic acid calcium having formula (I). The compound of formula (I) has adopted name "Rosuvastatin Calcium".

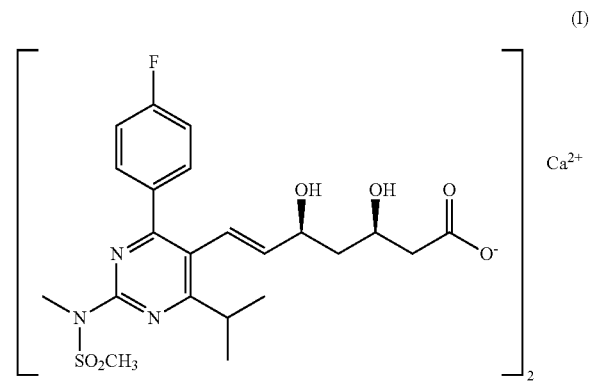

The present invention is also related to novel intermediates of formula (4) and formula (5) used in preparation of formula (I), and process of their preparation.

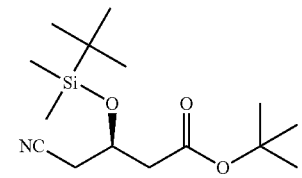

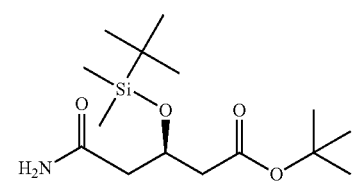

20 Claims, No Drawings

(56) References Cited

U.S. PATENT DOCUMENTS

2009/0124803 A1* 5/2009 Deshpande .......... C07D 239/42
544/322
2011/0124864 A1 5/2011 Chen

FOREIGN PATENT DOCUMENTS

| WO | 2006/091771 | 8/2006 |
| WO | 2007/041666 | 4/2007 |
| WO | 2008/130638 | 10/2008 |
| WO | 2008/130678 | 10/2008 |
| WO | 2012/063115 | 5/2012 |
| WO | 2013/080219 | 6/2013 |

OTHER PUBLICATIONS

J. Quirk et al., 2 Nature Reviews Drug Discovery, 769-779 (2003).*
European Patent Office, "International Search Report" and "Written Opinion", PCT Application No. PCT/IN2013/000702, Mar. 5, 2014.
European Patent Office, "Written Opinion", PCT Application No. PCT/IN2013/000702, Jun. 15, 2015.
European Patent Office, "International Preliminary Report on Patentability", PCT Application No. PCT/IN2013/000702, Sep. 21, 2015.

* cited by examiner

PROCESS FOR THE PREPARATION OF ROSUVASTATIN CALCIUM AND PREPARATION OF ITS NOVEL INTERMEDIATES

CROSS REFERENCE TO RELATED APPLICATIONS

This application is a national stage completion application of PCT Application No. PCT/IN2013/000702, filed Nov. 18, 2013, and claims the benefit of Indian Application No. 3174/CHE/2013, filed Jul. 16, 2013. Each of these applications is incorporated by reference herein.

FIELD OF THE INVENTION

The present invention relates to process for the preparation of 7-[4-(4-fluorophenyl)-6-isopropyl-2-(N-methyl-N-methylsulfonylamino)pyrimidin-5-yl]-(3R,5S)-dihydroxy-(E)-6-heptenoic acid calcium having formula (I). The compound of formula (I) has adopted name "Rosuvastatin Calcium".

(I)

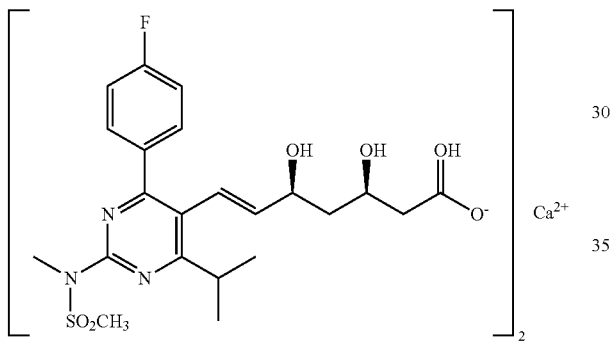

The present invention is also related to novel intermediates of formula (4) and formula (5) used in preparation of formula (I), and process of their preparation.

4

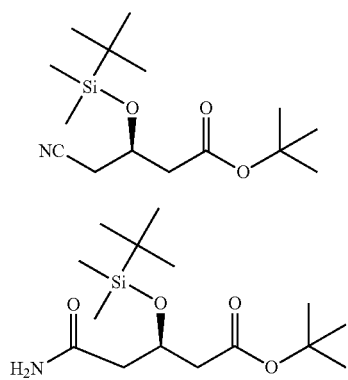

5

BACKGROUND OF THE INVENTION

Rosuvastatin calcium [7-[4-(4-fluorophenyl)-6-isopropyl-2-(N-methyl-N-methylsulfonylamino)pyrimidin-5-yl]-(3R,5S)-dihydroxy-(E)-6-heptenoic acid calcium] of formula (I) is disclosed in U.S. RE37314 assigned to Shionogi & Company Limited (Japan), an HMG-CoA reductase inhibitor that can lower LDL-cholesterol and triglycerides levels more effectively than first generation statin drugs. Rosuvastatin calcium is marketed under the name of CRESTOR.

The process for preparation of Rosuvastatin Calcium of formula (I) is disclosed in WO2006091771, US20070167625, WO2007041666, US20110124864, WO2012063115, US20060089501 and U.S. RE37314. The process disclosed in these references should undergo repeated purification procedures and also uses expensive reagents.

Therefore, it would be desirable and of paramount importance to have a process for the preparation of Rosuvastatin Calcium of formula (I), by employing inexpensive, readily available, easy to handle reagents. It would also be desirable to have a process that can be readily scaled up and which does not require a special purification step, thereby making it more suitable for industrial scale preparation.

SUMMARY OF THE INVENTION

In one aspect, the present invention relates to the novel intermediates of the formula (4) and formula (5), which are useful in the preparation of Rosuvastatin Calcium of formula (I)

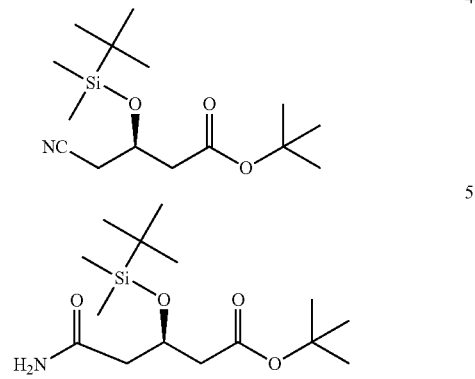

In another aspect, the present invention provides a process for preparation of novel intermediate of formula (4),

4

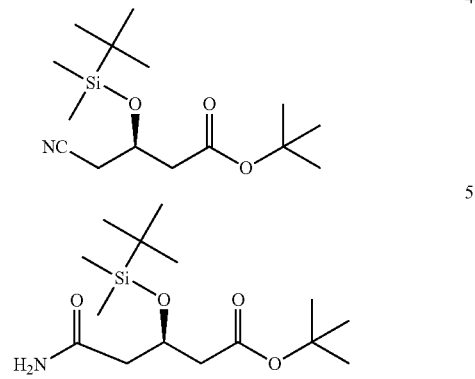

which comprises:
Step 1) reacting (R)-(−)-Ethyl 4-cyano-3-hydroxy butyrate of formula (1)

1

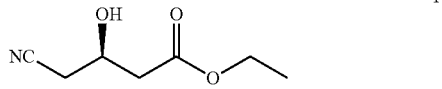

with tert-butyl dimethylsilyl chloride in presence of solvent and imidazole at a temperature in the range of 20° C. to 35° C. for the period of 18 hours to 22 hours to obtain (R)-(−)-Ethyl 4-cyano-3-(tert-butyldimethylsilyloxy) butyrate of formula (2);

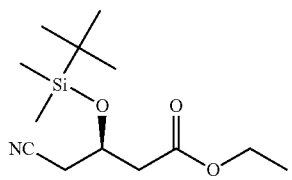

2

Step 2) hydrolysis of the (R)-(−)-Ethyl 4-cyano-3-(tertiarybutyl dimethylsilyloxy) butyrate of formula (2) in presence of solvent and a base at a temperature in the range of 8° C. to 18° C. for the period of 2 hours to 4 hours to obtain (R)-4-cyano-3-(tertiarybutyldimethylsilyloxy) butyric acid of formula (3);

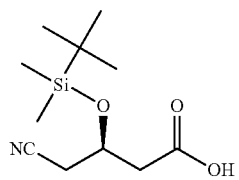

3

Step 3) esterifying the (R)-4-cyano-3-(tertiarybutyldimethylsilyloxy) butyric acid of formula (3) by using catalyst and di-tert-butyl dicarbonate in presence of solvent and a base at a temperature in the range of 20° C. to 35° C. for the period of 2 hours to 5 hours to obtain (R)-tertiary butyl 4-cyano-3-(tertiarybutyldimethylsilyloxy) butyrate of formula (4).

In another aspect, the present invention provides process for the preparation of novel intermediate of formula (5),

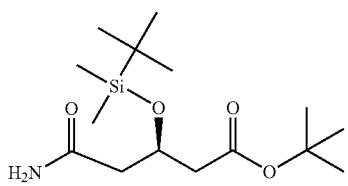

5 which comprises:

Step 1) reacting (R)-(−)-Ethyl 4-cyano-3-hydroxy butyrate of formula (1)

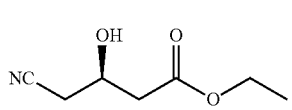

1 with tert-butyl dimethylsilyl chloride in presence of solvent and imidazole at a temperature in the range of 20° C. to 35° C. for the period of 18 hours to 22 hours to obtain (R)-(−)-Ethyl 4-cyano-3-(tert-butyldimethylsilyloxy) butyrate of formula (2);

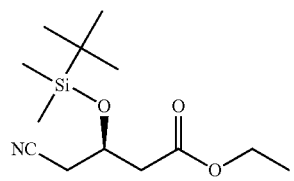

2

Step 2) hydrolysis of the (R)-(−)-Ethyl 4-cyano-3-(tertiarybutyldimethylsilyloxy) butyrate of formula (2) in presence of solvent and a base at a temperature in the range of 8° C. to 18° C. for the period of 2 hours to 4 hours to obtain (R)-4-cyano-3-(tertiarybutyldimethylsilyloxy) butyric acid of formula (3);

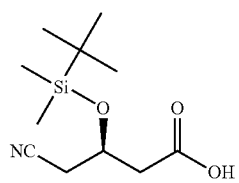

3

Step 3) esterifying the (R)-4-cyano-3-(tertiarybutyldimethylsilyloxy) butyric acid of formula (3) by using a catalyst and di-tert-butyl dicarbonate in presence of solvent and a base at a temperature in the range of 20° C. to 35° C. for the period of 2 hours to 5 hours to obtain (R)-tert-butyl 4-cyano-3-(tert-butyldimethylsilyloxy) butyrate of formula (4);

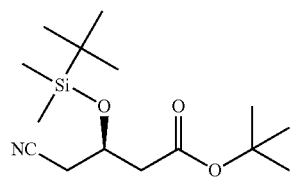

4

Step 4) converting the (R)-tert-butyl 4-cyano-3-(tert-butyldimethylsilyloxy) butyrate of formula (4) by using hydrogen peroxide in presence of solvent and a base at a temperature in the range of 20° C. to 35° C. for the period of 18 hours to 22 hours to obtain (R)-tert-butyl 4-carbamoyl-3-(tert-butyldimethylsilyloxy) butyrate of formula (5).

In another aspect, the present invention provides, process for the preparation of formula (I)

which comprises:

Step 1) reacting (R)-(−)-Ethyl 4-cyano-3-hydroxy butyrate of formula (1)

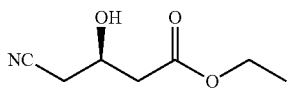

1 with tert-butyl dimethylsilyl chloride in presence of solvent and imidazole at a temperature in the range of 20° C. to 35° C. for the period of 18 hours to 22 hours to obtain (R)-(−)-Ethyl 4-cyano-3-(tert-butyldimethylsilyloxy) butyrate of formula (2);

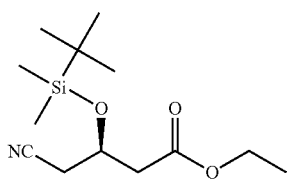

2

Step 2) hydrolysis of the (R)-(−)-Ethyl 4-cyano-3-(tert-butyldimethylsilyloxy) butyrate of formula (2) in presence of solvent and a base at a temperature in the range of 8° C. to 18° C. for the period of 2 hours to 4 hours to obtain (R)-4-cyano-3-(tert-butyldimethylsilyloxy) butyric acid of formula (3);

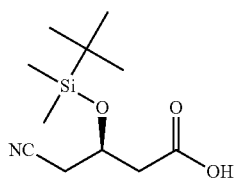

3

Step 3) esterifying (R)-4-cyano-3-(tert-butyldimethylsilyloxy) butyric acid of formula (3) by using a catalyst and di-tert-butyl dicarbonate in presence of solvent and a base at a temperature in the range of 20° C. to 35° C. for the period of 2 hours to 5 hours to obtain (R)-tertiary butyl 4-cyano-3-(tert-butyldimethylsilyloxy) butyrate of formula (4);

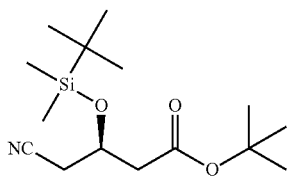

4

Step 4) converting (R)-tert-butyl 4-cyano-3-(tert-butyldimethylsilyloxy) butyrate of formula (4) by using hydrogen peroxide in presence of solvent and base at a temperature in the range of 20° C. to 35° C. for the period of 18 hours to 22 hours to obtain (R)-tertiarybutyl 4-carbamoyl-3-(tert-butyldimethylsilyloxy) butyrate of formula (5);

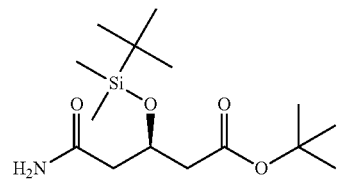

5

Step 5) converting (R)-tert-butyl 4-carbamoyl-3-(tert-butyldimethylsilyloxy) butyrate of formula (5) by using sodium hypochlorite in presence of solvent and a base at a temperature in the range of −5° C. to 10° C. for the period of 6 hours to 10 hours to obtain (R)-5-tert-butoxy-3-(tert-butyldimethylsilyloxy)-5-oxopentanoic acid of formula (6);

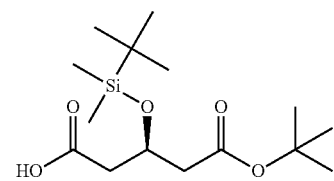

6

Step 6) converting the (R)-5-tert-butoxy-3-(tert-butyldimethylsilyloxy)-5-oxopentanoic acid of formula (6) by using ethylchloroformate in presence of solvent and a base at a temperature in the range of −35° C. to −55° C. for the period of 1 hour to 3 hours to obtain (R)-3-(tert-butyldimethylsilyloxy)-5-ethoxycarbonyloxy-5-oxo-pentanoic acid tert-butyl ester of formula (7);

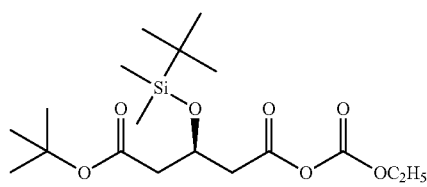

7

Step 7) converting the (R)-3-(tert-butyldimethylsilyloxy)-5-ethoxycarbonyloxy-5-oxo-pentanoic acid tert-butyl ester of formula (7) by using methyl triphenyl phosphonium bromide and organolithium reagent in presence of solvent at a temperature in the range of −5° C. to 5° C. for the period of 1 hour to 3 hours to obtain tert-butyl (3R)-3-(tert-butyldimethylsilyloxy)-5-oxo-6-triphenylphosphorylidene hexanoate of formula (8);

8

Step 8) reacting the tert-butyl(3R)-3-(tert-butyldimethylsilyloxy)-5-oxo-6-triphenylphosphorylidenehexanoate of formula (8) with 4-(4-Fluorophenyl)-6-isopropyl-2-(N-methyl-N-methylsulfonylamino)-5-pyrimidinecarboxaldehyde of formula (9)

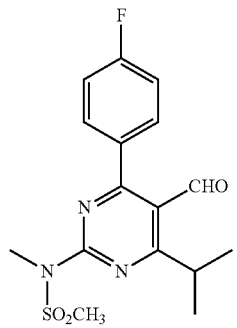

in presence of solvent at a temperature in the range of 75° C. to 90° C. for the period of 25 hours to 35 hours to obtain tertiary butyl 7-[4-(4-fluorophenyl)-6-isopropyl-2-(N-methyl-N-methylsulfonylamino) pyrimidin-5-yl]-(3R)-3-(tert-utyldimethylsilyloxy)-5-oxo-(E)-6-heptenoate of formula (10);

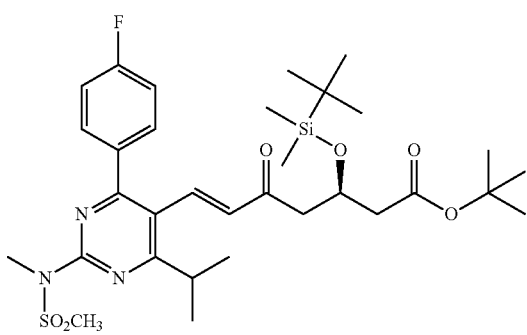

Step 9) deprotecting the tertiary butyl 7-[4-(4-fluorophenyl)-6-isopropyl-2-(N-methyl-N-methylsulfonylamino)pyrimidin-5-yl]-(3R)-3-(tert-butyldimethylsilyloxy)-5-oxo-(E)-6-heptenoate of formula (10) by using hydrochloric acid in presence of solvent at a temperature in the range of 15° C. to 30° C. for the period of 3 hours to 5 hours to obtain tertiary butyl 7-[4-(4-fluorophenyl)-6-isopropyl-2-(N-methyl-N-methylsulfonylamino) pyrimidin-5-yl]-(3R)-3-hydroxy-5-oxo-(E)-6-heptenoate of formula (11);

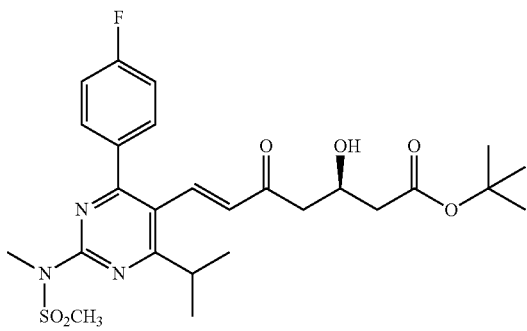

Step 10) reducing the tertiary butyl 7-[4-(4-fluorophenyl)-6-isopropyl-2-(N-methyl-N-methylsulfonylamino)pyrimidin-5-yl]-(3R)-3-hydroxy-5-oxo-(E)-6-heptenoate of formula (11) by using diethylmethoxy borane and sodium borohydride in presence of solvent at a temperature in the range of −75° C. to −82° C. for the period of 2 hours to 4 hours to obtain tertiary butyl 7-[4-(4-fluorophenyl)-6-isopropyl-2-(N-methyl-N-methylsulfonylamino)pyrimidin-5-yl]-(3R,5S)-dihydroxy-(E)-6-heptenoate of formula (12);

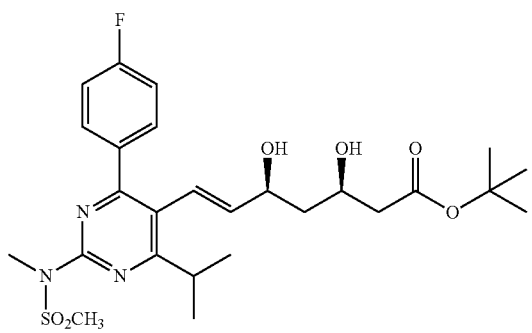

Step 11) converting the tertiary butyl 7-[4-(4-fluorophenyl)-6-isopropyl-2-(N-methyl-N-methylsulfonylamino)pyrimidin-5-yl]-(3R,5S)-dihydroxy-(E)-6-heptenoate of formula (12) by using aqueous sodium hydroxide in presence of solvent at a temperature in the range of 20° C. to 35° C. for the period of 2 hours to 4 hours to obtain 7-[4-(4-fluorophenyl)-6-isopropyl-2-(N-methyl-N-methylsulfonylamino) pyrimidin-5-yl]-(3R,5S)-dihydroxy-(E)-6-heptenoic acid sodium salt of formula (13);

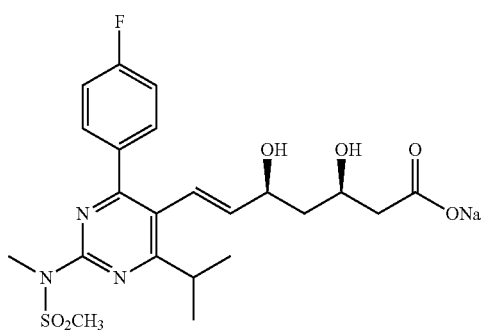

Step 12) converting the 7-[4-(4-fluorophenyl)-6-isopropyl-2-(N-methyl-N-methylsulfonylamino)pyrimidin-5-yl]-(3R,5S)-dihydroxy-(E)-6-heptenoic acid sodium salt of formula (13) by using water and calcium chloride at a temperature in the range of 15° C. to 30° C. for the period of 0.5 hour to 2 hours to obtain 7-[4-(4-fluorophenyl)-6-isopropyl-2-(N-methyl-N-methylsulfonylamino)pyrimidin-5-yl]-(3R,5S)-dihydroxy-(E)-6-heptenoic acid calcium salt of formula (I).

In another aspect, the present invention provides process for the preparation of Rosuvastatin Calcium of formula (I) by using inexpensive, readily available and easy to handle reagents.

In another aspect, the present invention provides process for the preparation of Rosuvastatin Calcium of formula (I), which can be readily scaled up and which does not require a special purification step to obtain pure Rosuvastatin Calcium of formula (I).

In yet another aspect, the present invention provides an improved process for the preparation of Rosuvastatin Calcium of formula (I), which is simple, convenient, economical and environment friendly.

DETAILED DESCRIPTION OF THE INVENTION

Accordingly, the present invention relates to novel intermediates of formula (4) and formula (5), which are useful for the preparation of Rosuvastatin Calcium of formula (I).

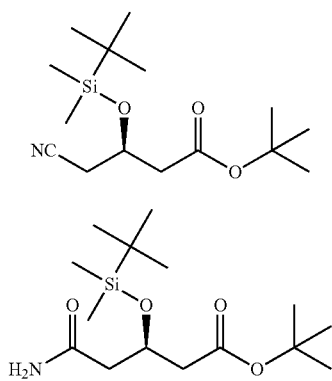

According to another aspect of the present invention, there is provided a process for the preparation of novel intermediate of formula (4),

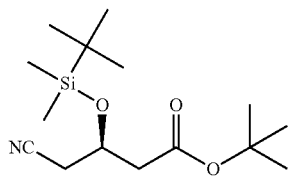

Scheme-1 illustrates the process for preparation of novel intermediate of formula (4).

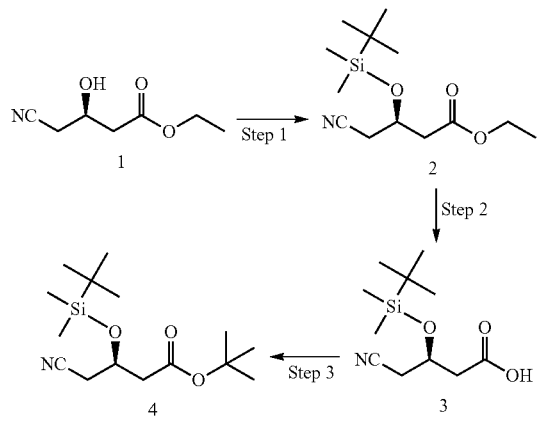

In Step 1 of the preparation, (R)-(−)-Ethyl 4-cyano-3-hydroxy butyrate of formula (1) is treated with tert-butyl dimethylsilyl chloride in presence of solvent and imidazole to obtain (R)-(−)-Ethyl 4-cyano-3-(tert-butyldimethylsily-loxy) butyrate of formula (2). The solvent used in the reaction can be selected from dichloromethane, dichloroethane or chloroform and preferably using dichloromethane. The reaction temperature may range from 20° C. to 35° C. and preferably at a temperature in the range from 20° C. to 25° C. The duration of the reaction may range from 18 hours to 22 hours, preferably for a period of 20 hours.

In Step 2 of the preparation, the above obtained (R)-(−)-Ethyl 4-cyano-3-(tert-butyldimethylsilyloxy) butyrate of formula (2) is hydrolysed in presence of solvent and base to obtain (R)-4-cyano-3-(tert-butyldimethylsilyloxy) butyric acid of formula (3). The solvent used in the reaction can be selected from methanol, dichloromethane, dichloroethane or chloroform and preferably using methanol. The base used in the reaction can be selected from potassium carbonate, sodium bicarbonate, sodium hydride or sodium hydroxide and preferably using sodium hydroxide. The reaction temperature may range from 8° C. to 18° C. and preferably at a temperature in the range from 10 to 15° C. The duration of the reaction may range from 2 hours to 4 hours, preferably for a period of 3 hours.

In Step 3 of the preparation, the above obtained (R)-4-cyano-3-(tert-butyldimethylsilyloxy) butyric acid of formula (3) is esterified by using catalyst and di-tert-butyl dicarbonate in presence of solvent and a base to obtain (R)-tertiary butyl 4-cyano-3-(tertiarybutyldimethylsilyloxy) butyrate of formula (4). The catalyst used in the reaction can be selected from 4-dimethylaminopyridine, tert-butyl ethyl fumarate or dicyclohexylcarbodiimide and preferably using 4-dimethylaminopyridine. The solvent used in the reaction can be selected from t-butanol, dichloromethane, dichloroethane or chloroform and preferably using t-butanol. The base used in the reaction can be selected from potassium carbonate, sodium bicarbonate, sodium hydride or sodium hydroxide and preferably using sodium hydroxide. The reaction temperature may range from 20° C. to 35° C. and preferably at a temperature in the range from 25° C. to 30° C. The duration of the reaction may range from 2 hours to 5 hours, preferably from a period of 3 hours to 4 hours.

According to another aspect of the present invention, there is provided a process for the preparation of novel intermediate of formula (5),

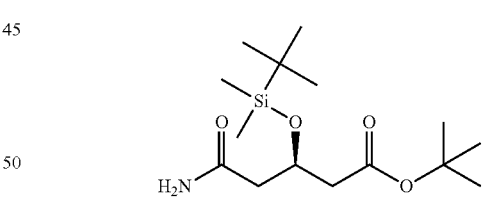

Scheme-2 illustrates the process for preparation of novel intermediate of formula (5).

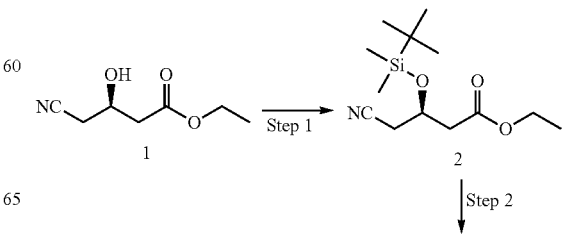

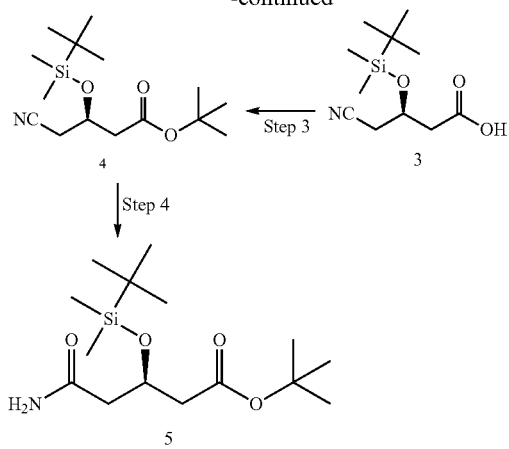

Scheme-2

In Step 1 of the preparation, (R)-(−)-Ethyl 4-cyano-3-hydroxy butyrate of the formula (1) is treated with tertiary-butyldimethylsilyl chloride in presence of solvent and imidazole to obtain (R)-(−)-Ethyl 4-cyano-3-(tert-butyldimethylsilyloxy) butyrate of formula (2). The solvent used in the reaction can be selected from dichloromethane, dichloroethane or chloroform and preferably using dichloromethane. The reaction temperature may range from 20° C. to 35° C. and preferably at a temperature in the range from 20° C. to 25° C. The duration of the reaction may range from 18 hours to 22 hours, preferably for a period of 20 hours.

In Step 2 of the preparation, the above obtained (R)-(−)-Ethyl-4-cyano-3-(tert-butyldimethylsilyloxy) butyrate of formula (2) is hydrolysed in presence of solvent and a base to obtain (R)-4-cyano-3-(tert-butyldimethylsilyloxy) butyric acid of formula (3).

The solvent used in the reaction can be selected from methanol, dichloromethane, dichloroethane or chloroform and preferably using methanol. The base used in the reaction can be selected from potassium carbonate, sodium bicarbonate, sodium hydride or sodium hydroxide and preferably using sodium hydroxide. The reaction temperature may range from 8° C. to 18° C. and preferably at a temperature in the range from 10 to 15° C. The duration of the reaction may range from 2 hours to 4 hours, preferably for a period of 3 hours.

In Step 3 of the preparation, the above obtained (R)-4-cyano-3-(tert-butyldimethylsilyloxy) butyric acid of formula (3) is esterified by using catalyst and di-tert-butyl dicarbonate) in presence of solvent and a base to obtain (R)-tertiary butyl 4-cyano-3-(tertiarybutyldimethylsilyloxy) butyrate of formula (4). The catalyst used in the reaction can be selected from 4-dimethylaminopyridine, tert-butyl ethyl fumarate or dicyclohexylcarbodiimide and preferably using 4-dimethylaminopyridine. The solvent used in the reaction can be selected from t-butanol, dichloromethane, dichloroethane or chloroform and preferably using t-butanol. The base used in the reaction can be selected from potassium carbonate, sodium bicarbonate, sodium hydride or sodium hydroxide and preferably using sodium hydroxide. The reaction temperature may range from 20° C. to 35° C. and preferably at a temperature in the range from 25° C. to 30° C. The duration of the reaction may range from 2 hours to 5 hours, preferably from a period of 3 hours to 4 hours.

In Step 4 of the preparation, the above obtained (R)-tertiary butyl 4-cyano-3-(tert-butyldimethylsilyloxy) butyrate of formula (4) is converted by using hydrogen peroxide in presence of solvent and a base to obtain (R)-tert-butyl 4-carbamoyl-3-(tert-butyldimethylsilyloxy) butyrate of formula (5). The solvent used in the reaction can be selected from ethanol, dichloromethane, dichloroethane or chloroform and preferably using ethanol. The base used in the reaction can be selected from potassium carbonate, sodium bicarbonate, sodium hydride or sodium hydroxide and preferably using sodium hydroxide. The reaction temperature may range from 20° C. to 35° C. and preferably at a temperature in the range from 28° C. to 30° C. The duration of the reaction may range from 18 hours to 22 hours, preferably for a period of 20 hours.

According to another aspect of the present invention, there is provided a process for the preparation of Rosuvastatin Calcium of formula (I).

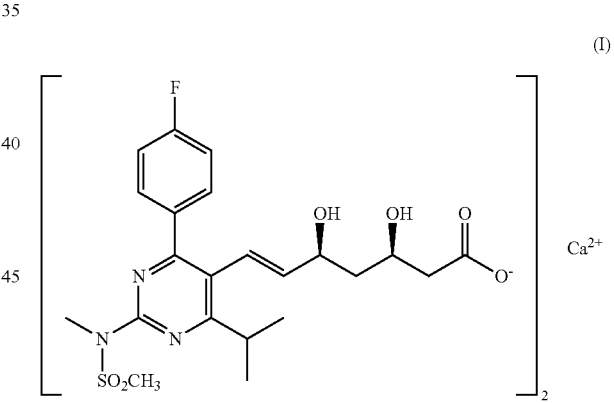

Scheme-3 illustrates the process for preparation of Rosuvastatin Calcium of formula (I)

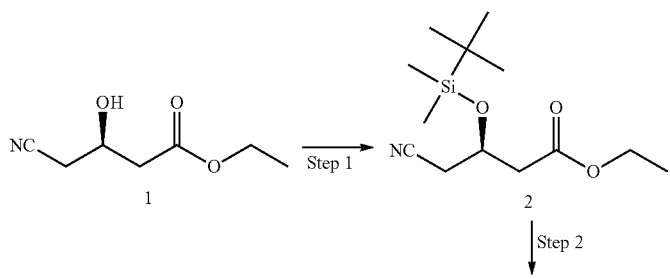

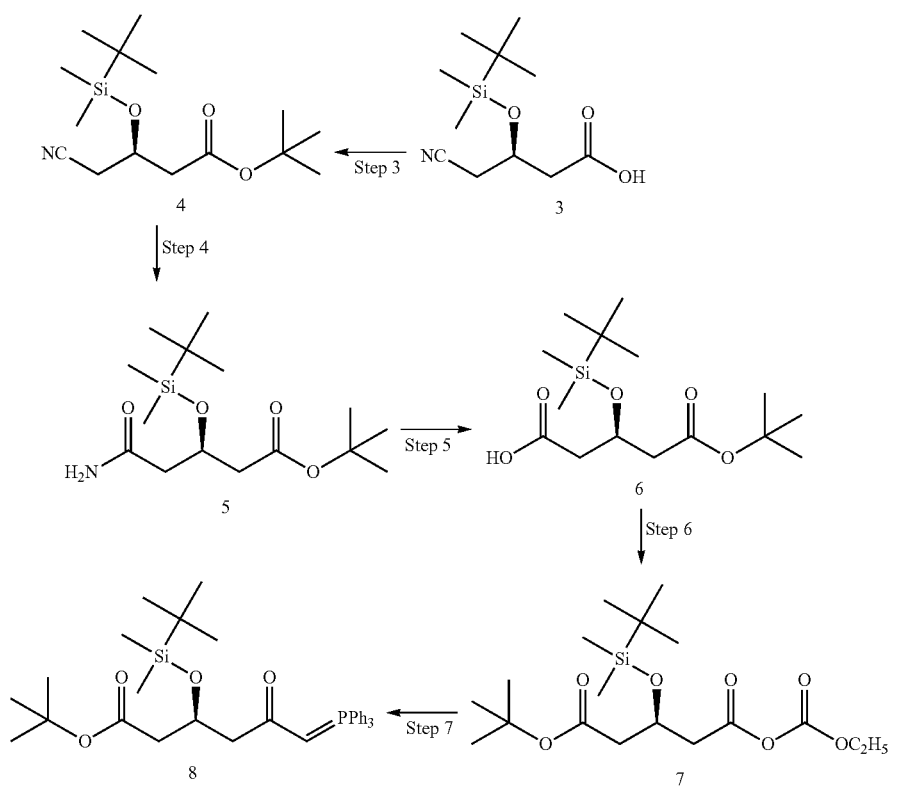
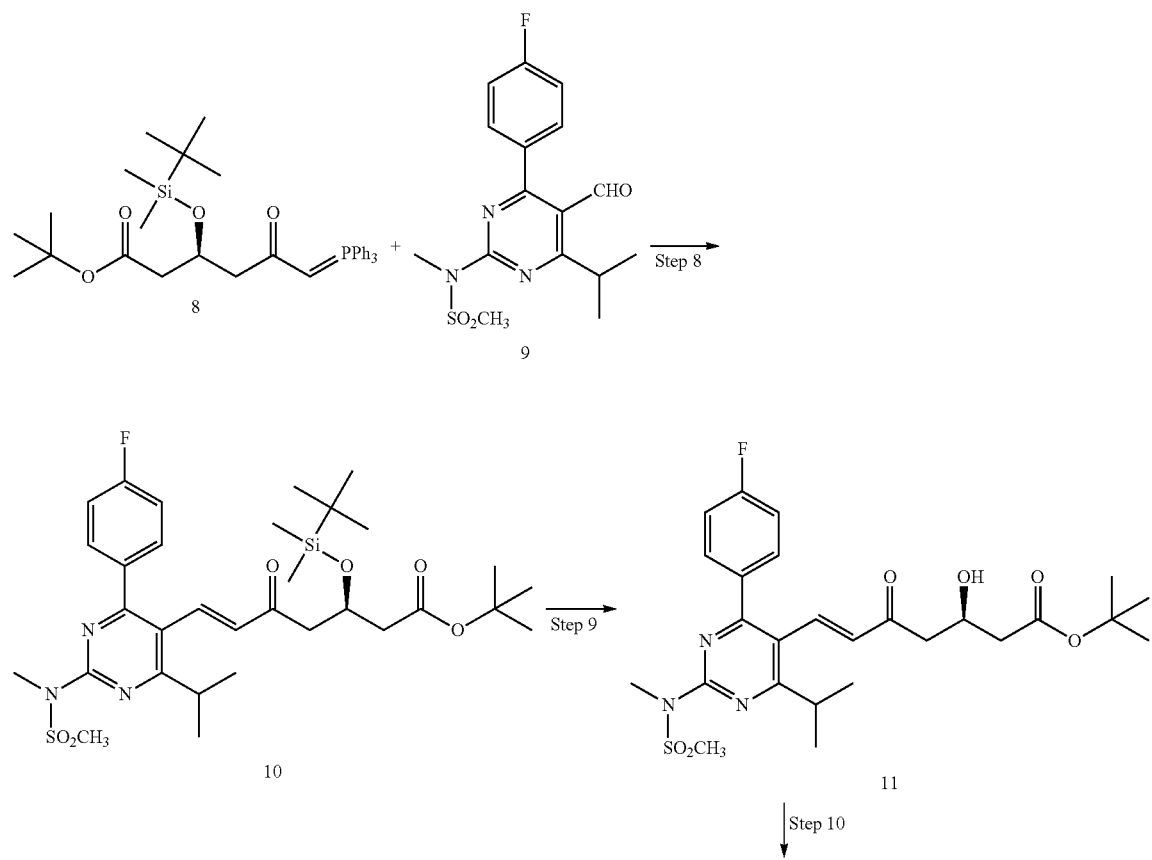

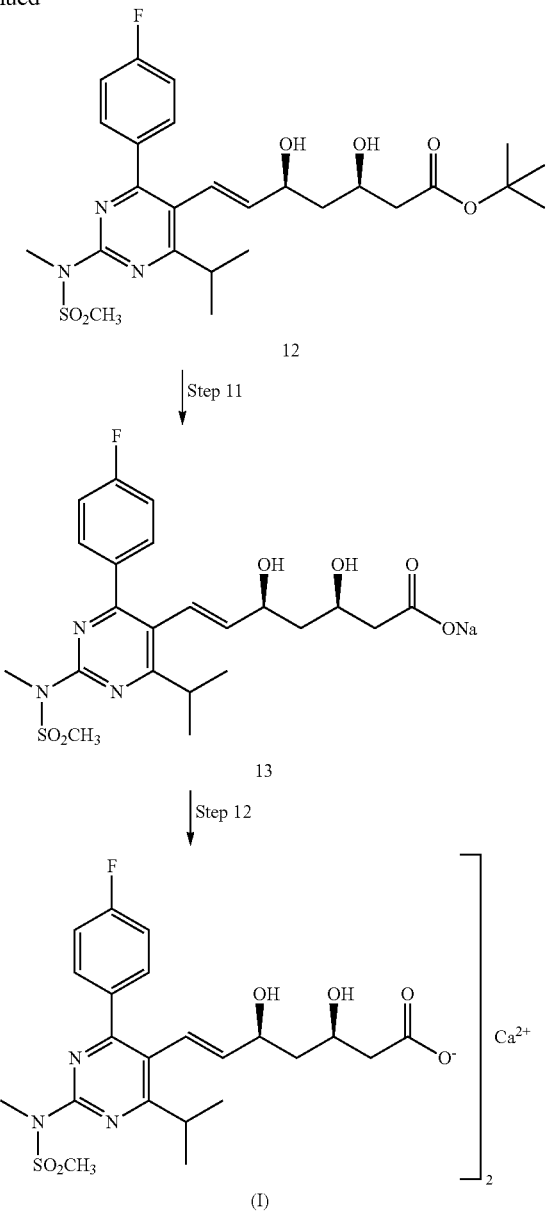

Scheme-3

In Step 1 of the preparation, (R)-(−)-Ethyl 4-cyano-3-hydroxy butyrate of formula (1) is treated with tert-butyl dimethylsilyl chloride in presence of solvent and imidazole to obtain (R)-(−)-Ethyl 4-cyano-3-(tert-butyldimethylsilyloxy) butyrate of formula (2). The solvent used in the reaction can be selected from dichloromethane, dichloroethane or chloroform and preferably using dichloromethane. The reaction temperature may range from 20° C. to 35° C. and preferably at a temperature in the range from 20° C. to 25° C. The duration of the reaction may range from 18 hours to 22 hours, preferably for a period of 20 hours.

In Step 2 of the preparation, the above obtained (R)-(−)-Ethyl 4-cyano-3-(tert-butyldimethylsilyloxy) butyrate of formula (2) is hydrolysed in presence of solvent and a base to obtain (R)-4-cyano-3-(tert-butyldimethylsilyloxy) butyric acid of formula (3). The solvent used in the reaction can be selected from methanol, dichloromethane, dichloroethane or chloroform and preferably using methanol. The base used in the reaction can be selected from potassium carbonate, sodium bicarbonate, sodium hydride or sodium hydroxide and preferably using sodium hydroxide. The reaction temperature may range from 8° C. to 18° C. and preferably at a temperature in the range from 10 to 15° C. The duration of the reaction may range from 2 hours to 4 hours, preferably for a period of 3 hours.

In Step 3 of the preparation, the above obtained (R)-4-cyano-3-(tert-butyldimethylsilyloxy) butyric acid of formula (3) is esterified by using catalyst and di-tert-butyl dicarbonate in presence of solvent and a base to obtain (R)-tertiary butyl 4-cyano-3-(tert-butyldimethylsilyloxy) butyrate of formula (4). The catalyst used in the reaction can be selected from 4-dimethylaminopyridine, tert-butyl ethyl fumarate or dicyclohexylcarbodiimide and preferably using 4-dimethylaminopyridine. The solvent used in the reaction can be selected from t-butanol, dichloromethane, dichloroethane or chloroform and preferably using t-butanol. The base used in the reaction can be selected from potassium carbonate, sodium bicarbonate, sodium hydride or sodium hydroxide and preferably using sodium hydroxide. The reaction temperature may range from 20° C. to 35° C. and preferably at a temperature in the range from 25° C. to 30° C. The duration of the reaction may range from 2 hours to 5 hours, preferably from a period of 3 hours to 4 hours.

In Step 4 of the preparation, the above obtained (R)-tertiary butyl 4-cyano-3-(tert-butyldimethylsilyloxy) butyrate of formula (4) is converted by using hydrogen peroxide in presence of solvent and a base to obtain (R)-tert-butyl 4-carbamoyl-3-(tert-butyldimethylsilyloxy) butyrate of formula (5). The solvent used in the reaction can be selected from ethanol, dichloromethane, dichloroethane or chloroform and preferably using ethanol. The base used in the reaction can be selected from potassium carbonate, sodium bicarbonate, sodium hydride or sodium hydroxide and preferably using sodium hydroxide. The reaction temperature may range from 20° C. to 35° C. and preferably at a temperature in the range from 28° C. to 30° C. The duration of the reaction may range from 18 hours to 22 hours, preferably for a period of 20 hours.

In Step 5 of the preparation, the above obtained (R)-tert-butyl4-carbamoyl-3-(tert-butyldimethylsilyloxy) butyrate of formula (5) is converted by using sodium hypochlorite in presence of solvent to obtain (R)-5-tert-butoxy-3-(tert-butyldimethylsilyloxy)-5-oxopentanoic acid of formula (6). The solvent used in the reaction can be selected from ethanol, dichloromethane, dichloroethane or chloroform and preferably using dichloromethane. The reaction temperature may range from −5° C. to 10° C. and preferably at a temperature in the range from 0° C. to 5° C. The duration of the reaction may range from 6 hours to 10 hours, preferably for a period of 8 hours.

In Step 6 of the preparation, the above obtained (R)-5-tertiarybutoxy-3-(tert-butyldimethylsilyloxy)-5-oxopentanoic acid of formula (6) is converted by using ethyl chloroformate in presence of solvent and a base to obtain (R)-3-(tert-butyldimethylsilyloxy)-5-ethoxycarbonyloxy-5-oxo-pentanoic acid tert-butyl ester of formula (7). The solvents used in the reaction can be selected from toluene, ethanol, dichloromethane, dichloroethane or chloroform and preferably using toluene. The base used in the reaction can be selected from triethyl amine, potassium carbonate, sodium bicarbonate, sodium hydride or sodium hydroxide and preferably using triethyl amine. The reaction temperature may range from −35° C. to −55° C. and preferably at a temperature in the range from −40° C. to −45° C. The duration of the reaction may range from 1 hour to 3 hours, preferably for a period of 2 hours.

In Step 7 of the preparation, the above obtained (R)-3-(tert-butyldimethylsilyloxy)-5-ethoxycarbonyloxy-5-oxopentanoic acid tert-butyl ester of formula (7) is converted by using methyl triphenyl phosphonium bromide and organolithium reagent in presence of solvent to obtain tert-butyl (3R)-3-(tert-butyldimethylsilyloxy)-5-oxo-6-triphenylphosphorylidenehexanoate of formula (8). The organolithium reagent is selected from n-butyllithium, sec-butyllithium or tert-butyllithium and preferably using n-butyllithium. The solvent used in the reaction can be selected from tetrahydrofuran, toluene, ethanol, dichloromethane, dichloroethane or chloroform and preferably using toluene and tetrahydrofuran. The reaction temperature may range from −5° C. to 5° C. and preferably at a temperature in the range from 0° C. to 5° C. The duration of the reaction may range from 1 hour to 3 hours, preferably for a period of 1.5 hours.

In Step 8 of the preparation, the above obtained tert-butyl-(3R)-3-(tert-butyldimethylsilyloxy)-5-oxo-6-triphenylphosphoranylidenehexanoate of formula (8) is reacted with 4-(4-Fluorophenyl)-6-isopropyl-2-(N-methyl-N-methylsulfonylamino)-5-pyrimidinecarboxaldehyde of formula (9) in presence of solvent to obtain tert-butyl 7-[4-(4-fluorophenyl)-6-isopropyl-2-(N-methyl-N-methylsulfonylamino)pyrimidin-5-yl]-(3R)-3-(tert-butyldimethylsilyloxy)-5-oxo-(E)-6-heptenoate of formula (10). The solvent used in the reaction can be selected from cyclohexane, toluene, ethanol, dichloromethane, dichloroethane or chloroform and preferably using cyclohexane. The reaction temperature may range from 75° C. to 90° C. and preferably at a temperature in the range from 80° C. to 82° C. The duration of the reaction may range from 25 hours to 35 hours, preferably for a period of 30 hours.

In Step 9 of the preparation, the above obtained tert-butyl 7-[4-(4-fluorophenyl)-6-isopropyl-2-(N-methyl-N-methylsulfonylamino)pyrimidin-5-yl]-(3R)-3-(tert-butyldimethylsilyloxy)-5-oxo-(E)-6-heptenoate of formula (10) is deprotected by using hydrochloric acid in presence of solvent to obtain tert-butyl 7-[4-(4-fluorophenyl)-6-isopropyl-2-(N-methyl-N-methylsulfonylamino)pyrimidin-5-yl]-(3R)-3-hydroxy-5-oxo-(E)-6-heptenoate of formula (11). The solvent used in the reaction can be selected from methanol, ethanol, dichloromethane, dichloroethane or chloroform and preferably using methanol. The reaction temperature may range from 15° C. to 30° C. and preferably at a temperature in the range from 20° C. to 25° C. The duration of the reaction may range from 3 hours to 5 hours, preferably for a period of 4 hours.

In Step 10 of the preparation, the above obtained tertiary butyl 7-[4-(4-fluorophenyl)-6-isopropyl-2-(N-methyl-N-methylsulfonylamino)pyrimidin-5-yl]-(3R)-3-hydroxy-5-oxo-(E)-6-heptenoate of formula (11) is reduced by using diethyl methoxy borane and sodium borohydride in presence of solvent to obtain tertiary butyl 7-[4-(4-fluorophenyl)-6-isopropyl-2-(N-methyl-N-methylsulfonylamino)pyrimidin-5-yl]-(3R,5S)-dihydroxy-(E)-6-heptenoate of formula (12). The solvent used in the reaction can be selected from tetrahydrofuran, methanol, ethanol, dichloromethane, dichloroethane or chloroform and preferably using methanol and tetrahydrofuran. The reaction temperature may range from −75° C. to −82° C. and preferably at a temperature in the range from −78° C. to −80° C. The duration of the reaction may range from 2 hours to 4 hours, preferably for a period of 3 hours.

In the Step 11 of the preparation, the above obtained tertiary butyl 7-[4-(4-fluorophenyl)-6-isopropyl-2-(N-methyl-N-methylsulfonylamino)pyrimidin-5-yl]-(3R,5S)-dihydroxy-(E)-6-heptenoate of formula (12) is converted in presence of solvent and base to 7-[4-(4-fluorophenyl)-6-isopropyl-2-(N-methyl-N-methylsulfonylamino)pyrimidin-5-yl]-(3R,5S)-dihydroxy-(E)-6-heptenoic acid sodium salt of formula (13). The solvent used in the reaction can be selected from water, toluene, ethanol, dichloromethane, dichloroethane or chloroform and preferably using ethanol and water. The base used in the reaction can be selected from potassium carbonate, sodium bicarbonate, sodium hydride or sodium hydroxide and preferably using sodium hydroxide. The reaction temperature may range from 20° C. to 35° C. and preferably at a temperature in the range from 25° C. to 30° C. The duration of the reaction may range from 2 hours to 4 hours, preferably for a period of 3 hours.

In the Step 12 of the preparation, the above obtained 7-[4-(4-fluorophenyl)-6-isopropyl-2-(N-methyl-N-methyl-sulfonylamino)pyrimidin-5-yl]-(3R,5S)-dihydroxy-(E)-6-heptenoic acid sodium salt of formula (13) is converted by using water and calcium chloride to 7-[4-(4-fluorophenyl)-6-isopropyl-2-(N-methyl-N-methylsulfonylamino) pyrimidin-5-yl]-(3R,5S)-dihydroxy-(E)-6-heptenoic acid calcium salt of formula (I). The reaction temperature may range from 15° C. to 30° C. and preferably at a temperature in the range from 20° C. to 25° C. The duration of the reaction may range from 0.5 hour to 2 hours, preferably for a period of 1 hour.

The details of the invention are given in the examples provided below, which are given to illustrate the invention only and therefore should not be construed to limit the scope of the invention.

EXAMPLE 1

Preparation of 7-[4-(4-fluorophenyl)-6-isopropyl-2-(N-methyl-N-methylsulfonylamino) pyrimidin-5-yl]-(3R,5S)-dihydroxy-(E)-6-heptenoic acid calcium salt Step 1: Preparation of (R)-(−)-Ethyl 4-cyano-3-(tert-butyldimethylsilyloxy) butyrate (2)

To a stirred solution of (R)-(−)-Ethyl 4-cyano-3-hydroxy butyrate (100 grams, 0.64 mol) in dichloromethane (400 mL) was added imidazole (50 grams, 0.735 mol) at 25° C. to 30° C. The reaction mixture was cooled to 20° C. to 25° C. and a solution of tert-butyldimethylsilyl chloride (101 grams, 0.67 mol in 100 mL of dichloromethane) was added in 1 hour at 20° C. to 25° C. The reaction mixture was gradually warmed to room temperature and stirred for 20 hours until the gas chromatography analysis revealed complete conversion of starting material. The reaction mixture was cooled to 10° C. to 15° C., filtered the salts and washed with dichloromethane. The resulting filtrate was washed with aqueous sodium hydroxide solution (2% w/w, 2×50 mL) and dried over anhydrous sodium sulfate (10 grams). The solvent was removed under reduced pressure to obtain the title compound (170 grams). Yield: 98%, Purity: 95%.

$^1$H-NMR (CDCl$_3$, δ ppm): 0.02 (s, 3H), 0.05 (s, 3H), 0.83 (s, 9H), 1.2 (t, 3H), 2.4-2.7 (dd, 2H), 2.75 (d, 2H), 4.0 (t, 2H), 4.3 (m, 1H);

Mass (m/z): 272.3 [M+H]$^+$.

Step 2: Preparation of (R)-4-cyano-3-(tert-butyldimethylsilyloxy) butyric acid (3)

To an ice cold (0° C. to 5° C.) solution of (R)-(−)-Ethyl 4-cyano-3-(tert-butyldimethylsilyloxy) butyrate (100 grams, 0.368 mol, obtained in the above step) in methanol (200 mL) was added an aqueous sodium hydroxide solution (22 grams, 0.55 mol in 200 mL of water). This reaction mixture was gradually warmed to 10° C. to 15° C. and stirred for 3 hours. The solvent was distilled off after adjusting the pH of reaction mass to 7.0 to 7.5 with concentrated hydrochloric acid (20 mL) to obtain the crude material. The pH of the crude material was adjusted to 12.0 to 12.5 with 10% aqueous sodium hydroxide solution (10 mL) and washed with dichloromethane (3×150 mL). The pH of the aqueous layer was adjusted to 2.0 to 2.2 with concentrated hydrochloric acid (40 mL) and extracted with dichloromethane (2×230 mL). The solvent was concentrated under reduced pressure to obtain the title product (78 grams). Yield: 87%, Purity: 98%.

$^1$H-NMR (CDCl$_3$, δ ppm): 0.01 (s, 3H), 0.04 (s, 3H), 0.83 (s, 9H), 2.36-2.7 (dd, 2H), 2.72 (d, 2H), 4.3 (m, 1H), 12.2 (b, 1H);

Mass (m/z): 444.4 [M+H]$^+$.

Step 3: Preparation of (R)-tert-butyl 4-cyano-3-(tert-butyldimethylsilyloxy) butyrate (4)

(R)-4-cyano-3-(tert-butyldimethylsilyloxy) butyric acid (100 grams, 0.411 mol, obtained in the above step) was taken in t-butanol (250 mL) at 25° C. to 30° C. The resulting solution was cooled to 10° C. to 15° C. and added sodium hydroxide powder (18.5 grams, 0.46 mol) and 4-dimethyl-aminopyridine (5 grams, 0.04 mol). This reaction mixture, was added a solution of ditertiarybutyl dicarbonate (180 grams, 0.0.82 mol in 150 mL of t-butanol) over a period of 1 hour at 8° C. to 10° C. The reaction mixture was slowly warmed to 25° C. to 30° C. and stirred for 3 hours to 4 hours. After completion of the reaction, the temperature of the reaction mixture was cooled to 15° C. to 20° C., by diluting with water (500 mL) and stirred for 10 minutes. The organic layer was separated and washed with brine solution. (2×100 mL). The organic layer was concentrated under reduced pressure to obtain the title compound (122 grams). Yield: 99%, Purity: 94%.

$^1$H-NMR (CDCl$_3$, δ ppm): 0.05 (s, 3H), 0.1 (s, 3H), 0.8 (s, 9H), 1.4 (s, 9H), 2.36-2.72 (dd, 2H), 2.73 (d, 2H), 4.3 (m, 1H);

Mass (m/z): 300.3 [M+H]$^+$.

Step 4: Preparation of (R)-tert-butyl 4-carbamoyl-3-(tert-butyldimethylsilyloxy) butyrate (5)

A mixture of (R)-tert-butyl 4-cyano-3-(tert-butyldimethylsilyloxy) butyrate (100 grams, 0.334 mol, obtained in the above step) and ethanol (300 mL) at 10° C. to 15° C., was added aqueous sodium hydroxide solution (45% w/w, 9 grams) and hydrogen peroxide (48% w/w, 190 grams, 2.68 mol). The reaction mass temperature was raised to 28° C. to 30° C. and stirred for 20 hours. After completion of the reaction, diluted with water (1200 mL) and cooled to −5° C. to −10° C. The resulting mixture was stirred for 3 hours. The resulting solid was filtered, washed with water (2×200 mL) and dried at 30° C. to 35° C. to obtain the title compound (81 grams). Yield: 76.5%, Purity: 98%.

$^1$H-NMR (CDCl$_3$, δ ppm): 0.03 (s, 6H), 0.8 (s, 9H), 1.38 (s, 9H), 2.16-2.49 (dd, 4H), 4.38 (m, 1H), 6.81 (b, 1H), 7.29 (b, 1H);

Mass (m/z): 318.3 [M+H]$^+$.

Step 5: Preparation of (R)-5-tert-butoxy-3-(tert-butyldimethylsilyloxy)-5-oxopentanoic acid (6)

To an ice cold (0° C. to 5° C.) solution of sodium hypochlorite (16% w/w, 572 grams, 1.23 mol) was added a solution of (R)-tertiarybutyl 4-carbamoyl-3-(tert-butyldimethylsilyloxy) butyrate (100 grams, 0.315 mol, obtained in the above step) in dichloromethane (500 mL). After stirring for 8 hours at 0° C. to 5° C., the pH of the reaction mixture was adjusted to 2.0 with hydrochloric acid (125 mL, 30% w/w). Two layers were separated and the aqueous layer was extracted with dichloromethane (100 mL). The combined organic layer was extracted with aqueous sodium hydroxide solution (8% w/w, 400 grams). The aqueous layer was diluted with water (200 mL) and adjusted the pH to 2.0 with hydrochloric acid (30 mL, 30% w/w) and extracted with dichloromethane (3×100 mL). The solvent was concentrated completely under vacuum to get the title compound (75 grams). Yield: 75%, Purity: 98%.

$^1$H-NMR (CDCl$_3$, δ ppm): 0.8 (s, 9H), 1.34-1.38 (s, 9H), 2.32-2.45 (dd, 4H), 4.38 (m, 1H), 12.2 (b, 1H);

Mass (m/z): 319.5 [M+H]$^+$.

Step 6: Preparation of (R)-3-(tert-butyldimethylsilyloxy)-5-ethoxycarbonyloxy-5-oxopentanoic acid tert-butyl ester (7)

The stirred solution of ethylchloroformate (37.5 grams, 0.346 mol) and toluene (1200 mL) was cooled to −40° C. to −45° C. under nitrogen atmosphere. A mixture of (R)-5-tert-butoxy-3-(tert-butyldimethylsilyloxy)-5-oxopentanoic acid (100 grams, 0.314 mol), triethylamine (37.5 grams, 0.37 mol) and toluene (200 mL) were added to the reaction mixture in 2 hours at −40° C. to −45° C. The reaction mass temperature was raised to 0° C. over a period of 2 hours and diluted with water (200 mL). The layers were separated and organic layer was washed with sodium bicarbonate solution (2% w/w, 200 mL) followed by brine solution (120 mL). The solvent was concentrated under vacuum to obtain the title compound (120 grams). Yield: 98.3%, Purity: 90%.

$^1$H-NMR (CDCl$_3$, δ ppm): 0.05 (s, 6H), 0.81 (s, 9H), 1.26 (t, 3H), 1.39-1.42 (s, 9H), 2.47 (dd, 2H), 2.66-2.68 (dd, 1H), 2.78-2.82 (dd, 1H), 4.23-4.28 (q, 2H), 4.42-4.45 (m, 1H);

Step 7: Preparation of Tert-butyl (3R)-3-(tert-butyldimethylsilyloxy)-5-oxo-6-triphenylphosphorylidenehexanoate (8)

To a stirred solution of methyl triphenyl phosphonium bromide (183 grams, 0.512 mol) in tetrahydrofuran (500 mL) at −60° C. was added n-butyl lithium solution (321 mL) in 2 hours. The reaction mixture was warmed to 0° C. over a period of 1.5 hours and then cooled to −60° C. A solution of (R)-3-(tert-butyldimethylsilyloxy)-5-ethoxycarbonyloxy-5-oxo pentanoic acid tert-butyl ester (100 grams, 0.256 mol, obtained in the above step) in toluene (280 mL) was added to the reaction mixture at −60° C. The reaction mass temperature was warmed to 0° C. over a period of 1.5 hour and diluted with water (100 mL). Two layers were separated and aqueous layer was extracted with toluene (120 mL). The combined organic layer was washed with sodium bicarbonate solution (8% w/w, 120 mL) followed by brine solution (120 mL), dried over anhydrous sodium sulphate.

The organic layer distilled off to obtain the title compound (135 grams). Yield: 55%, Purity: 60%.

$^1$H-NMR (CDCl$_3$, δ ppm): 0.05 (s, 6H), 0.82 (s, 9H), 1.41 (s, 9H), 2.38-2.5 (dd, 2H), 2.55-2.65 (dd, 2H), 4.5-4.52 (m, 1H), 7.26-7.63 (m, 15H);

Mass (m/z): 577.3 [M+H]$^+$.

Step 8: Preparation of Tertiary butyl 7-[4-(4-fluorophenyl)-6-isopropyl-2-(N-methyl-N-methylsulfonylamino)pyrimidin-5-yl]-(3R)-3-(tert-butyldimethylsilyloxy)-5-oxo-(E)-6-heptenoate (10)

4-(4-Fluorophenyl)-6-isopropyl-2-(N-methyl-N-methylsulfonylamino)-5-pyrimidinecarboxaldehyde (65 grams, 0.185 mol, obtained in the above step) was taken in cyclohexane (600 mL) and was stirred at room temperature. To the resulting mixture, tert-butyl-(3R)-3-(tert-butyldimethylsilyloxy)-5-oxo-6-triphenylphosphoranylidenehexanoate (185 grams, 0.193 mol) was added. The reaction mixture temperature was raised to 80° C. to 82° C. and stirred for 30 hours until the High Performance Liquid Chromatography analysis revealed complete conversion of starting material. The reaction mixture was cooled to 0° C., filtered the undissolved material and the filtrate was concentrated under vacuum at below 50° C. to obtain the title compound (189 grams). Yield: 97.5%, Purity: 62.2%.

$^1$H-NMR (CDCl$_3$, δ ppm): 0.01 (s, 3H), 0.06 (s, 3H), 0.83 (s, 9H), 1.27-1.29 (d, 6H), 1.42-1.45 (s, 9H), 2.39-2.4 (d, 2H), 2.74-2.76 (d, 2H), 3.35-3.38 (m, 1H), 3.51 (s, 3H), 3.57 (s, 3H), 4.52-4.55 (m, 1H), 6.14-6.18 (d, 1H) 7.1-7.4 (m, 2H), 7.57-7.64 (m, 2H);

Mass (m/z): 650.7 [M+H]$^+$.

Step 9: Preparation of Tertiary butyl 7-[4-(4-fluorophenyl)-6-isopropyl-2-(N-methyl-N-methylsulfonylamino)pyrimidin-5-yl]-(3R)-3-hydroxy-5-oxo-(E)-6-heptenoate (11)

To a stirred solution of tert-butyl 7-[4-(4-fluorophenyl)-6-isopropyl-2-(N-methyl-N-methylsulfonylamino)pyrimidin-5-yl]-(3R)-3-(tert-butyldimethylsilyloxy)-5-oxo-(E)-6-heptenoate (188 grams, obtained in the above step) in methanol (600 mL) at 10° C. to 15° C., was added a solution of concentrated hydrochloric acid (24 mL) slowly over a period of 30 minutes. The reaction mixture was gradually warmed to 20° C. to 25° C. and stirred for 4 hours at 20° C. to 25° C. The solvent was distilled off after adjusting the pH to 6.5 to 7.0 with sodium bicarbonate (17 grams), water (115 mL) was added and extracted with methyl tertiary butyl ether (2×200 mL). The methyl tertiary butyl ether layer was washed with sodium bicarbonate solution (230 mL, 8% w/w) followed by brine solution (115 mL), dried over anhydrous sodium sulphate. The solvent was removed under vacuum at below 50° C. to obtain the title product (189 grams). Yield: 92.8%, Purity: 49.13%.

$^1$H-NMR (CDCl$_3$, δ ppm): 1.18-1.21 (d, 6H), 1.4-1.45 (s, 9H), 2.42-2.43 (d, 2H), 2.68-2.72 (m, 2H), 3.33-3.37 (m, 1H), 3.47 (b, 1H), 3.51 (s, 3H), 3.58 (s, 3H), 4.52 (m, 1H), 6.14-6.18 (d, 1H), 7.1-7.4 (m, 2H), 7.57-7.64 (m, 2H);

Mass (m/z): 536.6 [M+H]$^+$.

Step 10: Preparation of Tertiary butyl 7-[4-(4-fluorophenyl)-6-isopropyl-2-(N-methyl-N-methylsulfonylamino)pyrimidin-5-yl]-(3R,5S)-dihydroxy-(E)-6-heptenoate (12)

Tertiary butyl 7-[4-(4-fluorophenyl)-6-isopropyl-2-(N-methyl-N-methylsulfonyl amino) pyrimidin-5-yl]-(3R)-3-hydroxy-5-oxo-(E)-6-heptenoate (188 grams, 0.172 mol, obtained in the above step) was taken in tetrahydrofuran (700 mL) and methanol (174 mL) at 25° C. under nitrogen atmosphere. The resulting mixture was cooled to −78° C. to −80° C. and diethylmethoxyborane (1M) in tetrahydrofuran solution (178 mL) was added to the reaction mixture followed by sodium borohydride (6.8 grams, 0.18 mol) over a period of 1 hour at −78° C. to −80° C. After stirring for 3 hours at −78° C. to −80° C., acetic acid (20 grams, 0.33 mol) was slowly added in 45 minutes. The reaction mixture was warmed to −10° C. to −15° C. and added ethyl acetate (472 mL) and water (472 mL). The temperature of the resulting mixture was raised to 25° C. and separated the layers. The aqueous layer was extracted with ethyl acetate (50 mL). The combined organic layer was washed with sodium bicarbonate solution (2×270 grams) followed by brine solution (2×270 mL). The solvent was distilled off at below 50° C. under vacuum to obtain the title compound (153 grams). Yield: 77.2%, Purity: 46.6%.

¹H-NMR (CDCl₃, δ ppm): 1.24-1.34 (d, 6H), 1.46 (s, 9H), 1.53 (m, 2H), 2.36-2.38 (d, 2H), 3.35 (m, 1H), 3.51 (s, 3H), 3.58 (s, 3H), 3.8 (b, 2H), 4.16 (m, 1H), 4.44 (m, 1H), 5.42-5.47 (dd, 1H), 6.6-6.64 (d, 1H), 7.0 (t, 2H), 7.62-7.65 (dd, 2H);
Mass (m/z): 538.4 [M+H]⁺.

Step 11: Preparation of sodium salt of 7-[4-(4-fluorophenyl)-6-isopropyl-2-(N-methyl-N-methylsulfonylamino)pyrimidin-5-yl]-(3R,5S)-dihydroxy-(E)-6-heptenoic acid (13)

To a stirred solution of tertiary butyl 7-[4-(4-fluorophenyl)-6-isopropyl-2-(N-methyl-N-methylsulfonylamino)pyrimidin-5-yl]-(3R,5S)-dihydroxy-(E)-6-heptenoate (152 grams, obtained in the above step) in ethanol (208 mL) and water (125 mL) was added 45% aqueous sodium hydroxide solution (20.5 grams). After stirring for 3 hours at 25° C. to 30° C., solvent was completely removed under vacuum and diluted with water (250 mL). The aqueous layer was washed with methyl tert-butyl ether (3×250 mL) and the aqueous layer was completely removed under vacuum to obtain the crude product. The resulting crude material was added methyl tert-butyl ether (1500 mL) and cooled to 0° C. The resulting mixture was stirred for 15 hours at 0° C., filtered and washed with methyl tert-butyl ether (2×100 mL), dried at 45° C. to 50° C. to obtain the title compound (56 grams). Yield: 78%.
¹H-NMR (CDCl₃, δ ppm): 1.19 (d, 6H), 1.27 (m, 1H), 1.47 (m, 1H), 1.83-1.88 (m, 1H), 2.02-2.06 (m, 1H), 3.43 (s, 3H), 3.53 (s, 3H), 3.6 (m, 1H), 4.18 (m, 1H), 5.14 (b, 1H), 5.49-5.53 (dd, 1H), 6.46-6.5 (dd, 1H), 6.8 (b, 1H), 7.24-7.28 (m, 2H), 7.7 (m, 2H); Mass (m/z): 482.5 [M+H]⁺.

Step 12: Preparation of 7-[4-(4-fluorophenyl)-6-isopropyl-2-(N-methyl-N-methylsulfonylamino)pyrimidin-5-yl]-(3R,5S)-dihydroxy-(E)-6-heptenoic acid calcium salt (I)

7-[4-(4-fluorophenyl)-6-isopropyl-2-(N-methyl-N-methylsulfonylamino)pyrimidin-5-yl]-(3R,5S)-dihydroxy-(E)-6-heptenoic acid sodium salt (55 grams, 0.109 mol, obtained in the above step) was taken in water (550 mL) and was added calcium chloride solution (15 grams, 0.135 mol in water (60 mL) over a period of 1 hour at 20° C. to 25° C. The reaction mixture was stirred for 2 hours, filtered and washed with water, dried at 40° C. to 45° C. under vacuum to obtain the title compound (50 grams). Yield: 91.5%.
¹H-NMR (CDCl₃, δ ppm for C22H27FN3O6S 0.5 Ca): 1.18 (d, 6H), 1.31 (m, 1H), 1.5 (m, 1H), 2.0-2.18 (m, 2H), 3.41 (s, 3H), 3.52 (s, 3H), 3.8 (m, 1H), 4.19 (m, 1H), 5.08 (b, 1H), 5.49 (dd, 1H), 5.67 (b, 1H), 6.51 (dd, 1H), 7.21-7.25 (m, 2H), 7.67-7.7 (m, 2H);
Mass (m/z): 482.5 [M+H]⁺.

We claim:
1. A process for preparation of the compound of formula (4),

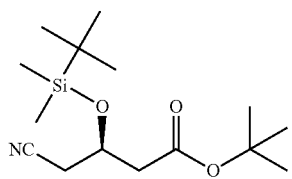

4 which comprises the steps of:
Step 1) reacting (R)-(−)-Ethyl 4-cyano-3-hydroxy butyrate of formula (1)

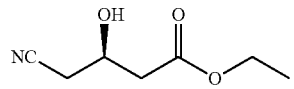

1 with tertiarybutyldimethylsilyl chloride in presence of solvent, selected from the group consisting of dichloromethane, dichloroethane and chloroform, and imidazole at a temperature in the range of 20° C. to 35° C. for the period of 18 hours to 22 hours to obtain (R)-(−)-Ethyl 4-cyano-3-(tertiarybutyldimethylsilyloxy) butyrate of formula (2);

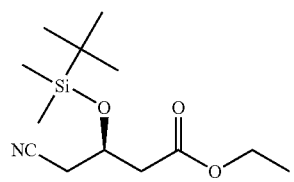

2

Step 2) hydrolysing the (R)-(−)-Ethyl 4-cyano-3-(tert-butyldimethylsilyloxy) butyrate of formula (2) in presence of solvent, selected from the group consisting of methanol, dichloromethane, dichloroethane and chloroform, and a base, selected from the group consisting of potassium carbonate, sodium bicarbonate, sodium hydride and sodium hydroxide, at a temperature in the range of 8° C. to 18° C. for the period of 2 hours to 4 hours to obtain (R)-4-cyano-3-(tert-butyldimethylsilyloxy) butyric acid of formula (3);

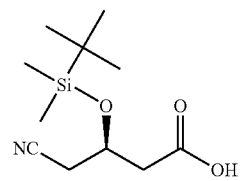

3

Step 3) esterifying (R)-4-cyano-3-(tert-butyldimethylsilyloxy) butyric acid of formula (3) by using catalyst, selected from the group consisting of 4-dimethylaminopyridine, tert-butyl ethyl fumarate and dicyclohexylcarbodiimide, and di-tert-butyl dicarbonate in presence of solvent, selected from the group consisting of t-butanol, dichloromethane, dichloroethane and chloroform, and a base, selected from the group consisting of potassium carbonate, sodium bicarbonate, sodium hydride and sodium hydroxide, at a temperature in the range of 20° C. to 35° C. for the period of 2 hours to 5 hours to obtain (R)-tertiary butyl 4-cyano-3-(tert-butyldimethylsilyloxy) butyrate of formula (4).

2. A process for preparation of the compound of formula (5),

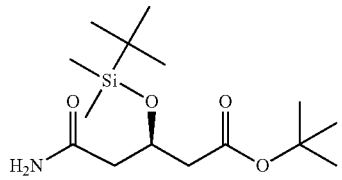

5 which comprises the steps of:
Step 1) reacting (R)-(−)-Ethyl 4-cyano-3-hydroxy butyrate of the formula (1)

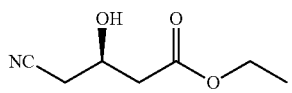

1 with tert-butyl dimethylsilyl chloride in presence of solvent, selected from the group consisting of dichloromethane, dichloroethane and chloroform, and imidazole at a temperature in the range of 20° C. to 35° C. for the period of 18 hours to 22 hours to obtain (R)-(−)-Ethyl 4-cyano-3-(tertiarybutyldimethylsilyloxy) butyrate of formula (2);

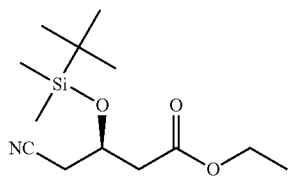

2

Step 2) hydrolysing the (R)-(−)-Ethyl 4-cyano-3-(tertiarybutyldimethylsilyloxy) butyrate of formula (2) in presence of solvent, selected from the group consisting of methanol, dichloromethane, dichloroethane and chloroform, and a base, selected from the group consisting of potassium carbonate, sodium bicarbonate, sodium hydride and sodium hydroxide, at a temperature in the range of 8° C. to 18° C. for the period of 2 hours to 4 hours to obtain (R)-4-cyano-3-(tert-butyldimethylsilyloxy) butyric acid of formula (3);

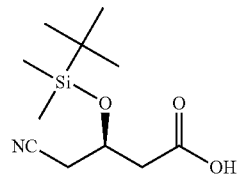

3

Step 3) esterifying the (R)-4-cyano-3-(tert-butyldimethylsilyloxy) butyric acid of formula (3) by using catalyst, selected from the group consisting of 4-dimethylaminopyridine, tert-butyl ethyl fumarate and dicyclohexylcarbodiimide, and di-tert-butyl dicarbonate in presence of solvent, selected from the group consisting of t-butanol, dichloromethane, dichloroethane and chloroform, and a base, selected from the group consisting of potassium carbonate, sodium bicarbonate, sodium hydride and sodium hydroxide, at a temperature in the range of 20° C. to 35° C. for the period of 2 hours to 5 hours to obtain (R)-tertiary butyl 4-cyano-3-(tert-butyldimethylsilyloxy) butyrate of formula (4);

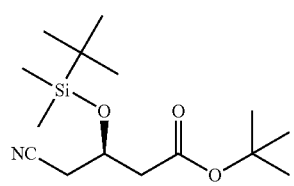

4

Step 4) converting the (R)-tert-butyl 4-cyano-3-(tert-butyldimethylsilyloxy) butyrate of formula (4) by using hydrogen peroxide in presence of solvent, selected from the group consisting of ethanol, dichloromethane, dichloroethane and chloroform, and a base, selected from the group consisting of potassium carbonate, sodium bicarbonate, sodium hydride and sodium hydroxide, at a temperature in the range of 20° C. to 35° C. for the period of 18 hours to 22 hours to obtain (R)-tert-butyl 4-carbamoyl-3-(tert-butyldimethylsilyloxy) butyrate of formula (5).

3. A process for the preparation of Rosuvastatin Calcium of formula (I),

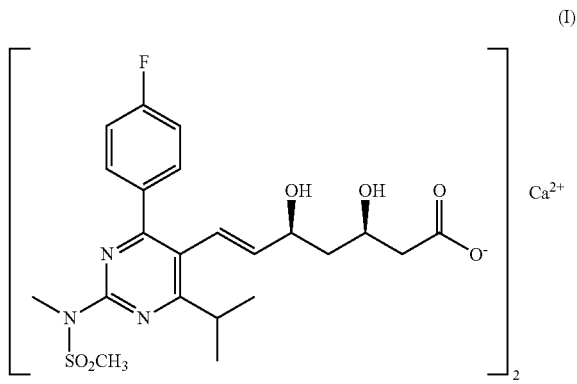

(I)

which comprises the steps of:
Step 1) reacting (R)-(−)-Ethyl 4-cyano-3-hydroxy butyrate of formula (1)

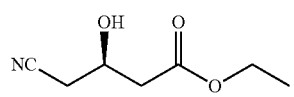

1 with tert-butyl dimethylsilyl chloride in presence of solvent, selected from the group consisting of dichloromethane, dichloroethane and chloroform, and imidazole at a temperature in the range of 20° C. to 35° C. for the period of 18 hours to 22 hours to obtain (R)-(−)-Ethyl 4-cyano-3-(tert-butyldimethylsilyloxy) butyrate of formula (2);

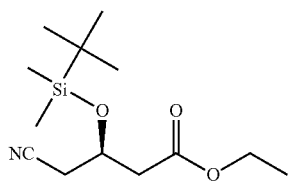

2

Step 2) hydrolysing the (R)-(−)-Ethyl 4-cyano-3-(tertiarybutyldimethylsilyloxy) butyrate of formula (2) in presence of solvent, selected from the group consisting of methanol, dichloromethane, dichloroethane and chloroform, and base, selected from the group consisting of potassium carbonate, sodium bicarbonate, sodium hydride and sodium hydroxide, at a temperature in the range of 8° C. to 18° C. for the period of 2 hours to 4 hours to obtain (R)-4-cyano-3-(tertiarybutyldimethylsilyloxy) butyric acid of formula (3);

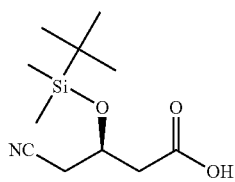

3

Step 3) esterifying (R)-4-cyano-3-(tert-butyldimethylsilyloxy) butyric acid of formula (3) by using catalyst, selected from the group consisting of 4-dimethylaminopyridine, tert-butyl ethyl fumarate and dicyclohexylcarbodiimide, and di-tert-butyl dicarbonate in presence of solvent, selected from the group consisting of t-butanol, dichloromethane, dichloroethane and chloroform, and a base, selected from the group consisting of potassium carbonate, sodium bicarbonate, sodium hydride and sodium hydroxide, at a temperature in the range of 20° C. to 35° C. for the period of 2 hours to 5 hours to obtain (R)-tertiary butyl 4-cyano-3-(tertiarybutyldimethylsilyloxy) butyrate of formula (4);

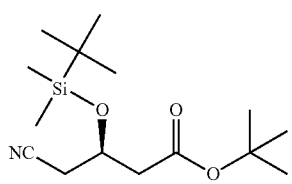

4

Step 4) converting the (R)-tertiary butyl 4-cyano-3-(tert-butyldimethylsilyloxy) butyrate of formula (4) by using hydrogen peroxide in presence of solvent, selected from the group consisting of ethanol, dichloromethane, dichloroethane and chloroform, and a base, selected from the group consisting of potassium carbonate, sodium bicarbonate, sodium hydride and sodium hydroxide, at a temperature in the range of 20° C. to 35° C. for the period of 18 hours to 22 hours to obtain (R)-tert-butyl 4-carbamoyl-3-(tert-butyldimethylsilyloxy) butyrate of formula (5);

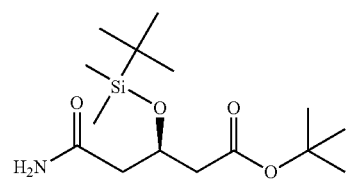

5

Step 5) converting the (R)-tert-butyl 4-carbamoyl-3-(tert-butyldimethylsilyloxy) butyrate of formula (5) by using sodium hypochlorite in presence of solvent, selected from the group consisting of ethanol, dichloromethane, dichloroethane and chloroform, and a base at a temperature in the range of −5° C. to 10° C. for the period of 6 hours to 10 hours to obtain (R)-5-tert-butoxy-3-(tert-butyldimethylsilyloxy)-5-oxopentanoic acid of formula (6);

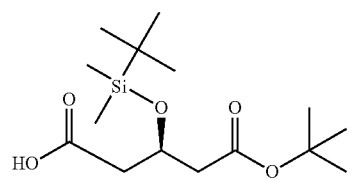

6

Step 6) converting the (R)-5-tert-butoxy-3-(tert-butyldimethylsilyloxy)-5-oxopentanoic acid of formula (6) by using ethyl chloroformate in presence of solvent, selected from the group consisting of toluene, ethanol, dichloromethane, dichloroethane and chloroform, and a base, selected from the group consisting of triethyl amine, potassium carbonate, sodium bicarbonate, sodium hydride or sodium hydroxide, at a temperature in the range of −35° C. to −55° C. for the period of 1 hour to 3 hours to obtain (R)-3-(tert-butyldimethylsilyloxy)-5-ethoxycarbonyloxy-5-oxo-pentanoic acid tert-butyl ester of formula (7);

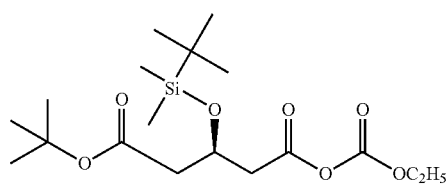

7

Step 7) converting the (R)-3-(tert-butyldimethylsilyloxy)-5-ethoxycarbonyloxy-5-oxo-pentanoic acid tert-butyl ester of formula (7) by using methyl triphenyl phosphonium bromide and organolithium reagent, selected from the group consisting of n-butyllithium, sec-butyllithium and tert-butyllithium, in presence of solvent, selected from the group consisting of tetrahydrofuran, toluene, ethanol, dichloromethane, dichloroethane and chloroform, at a temperature in the range of −5° C. to 5° C. for the period of 1 hour to 3 hours to obtain tert-butyl(3R)-3-(tert-butyldimethylsilyloxy)-5-oxo-6-triphenylphosphorylidene hexanoate of formula (8);

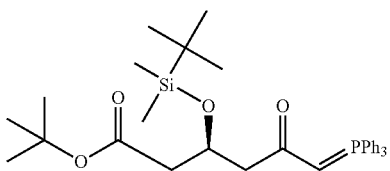

8

Step 8) reacting the tert-butyl(3R)-3-(tert-butyldimethyl-silyloxy)-5-oxo-6-triphenylphosphorylidene hexanoate of formula (8) with 4-(4-Fluorophenyl)-6-isopropyl-2-(N-methyl-N-methylsulfonylamino)-5-pyrimidinecarboxaldehyde of formula (9)

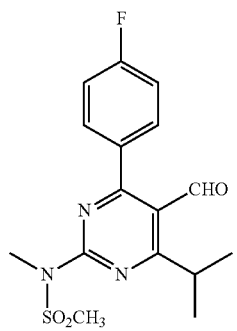

9 in presence of solvent, selected from the group consisting of cyclohexane, toluene, ethanol, dichloromethane, dichloroethane and chloroform, at a temperature in the range of 75° C. to 90° C. for the period of 25 hours to 35 hours to obtain tert-butyl 7-[4-(4-fluorophenyl)-6-isopropyl-2-(N-methyl-N-methylsulfonylamino)pyrimidin-5-yl]-(3R)-3-(tert-butyldimethylsilyloxy)-5-oxo-(E)-6-heptenoate of formula (10);

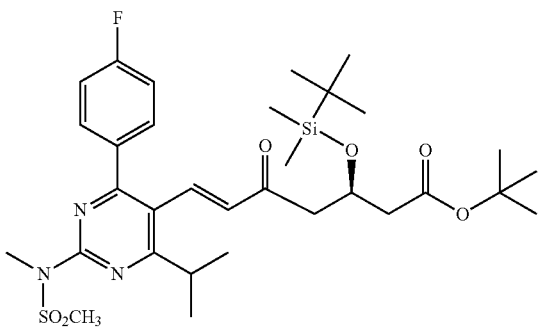

10

Step 9) deprotecting the tert-butyl 7-[4-(4-fluorophenyl)-6-isopropyl-2-(N-methyl-N-methylsulfonylamino)pyrimidin-5-yl]-(3R)-3-(tert-butyldimethylsilyloxy)-5-oxo-(E)-6-heptenoate of formula (10) by using hydrochloric acid in presence of solvent, selected from the group consisting of methanol, ethanol, dichloromethane, dichloroethane and chloroform, at a temperature in the range of 15° C. to 30° C. for the period of 3 hours to 5 hours to obtain tert-butyl 7-[4-(4-fluorophenyl)-6-isopropyl-2-(N-methyl-N-methylsulfonylamino)pyrimidin-5-yl]-(3R)-3-hydroxy-5-oxo-(E)-6-heptenoate of formula (11);

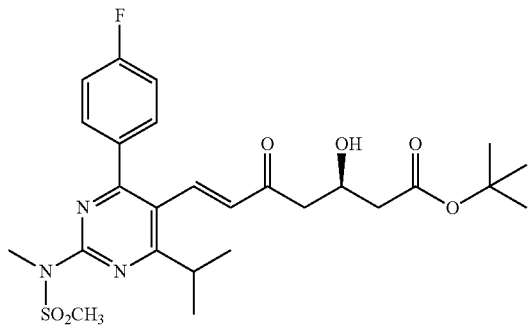

11

Step 10) reducing the tertiary butyl 7-[4-(4-fluorophenyl)-6-isopropyl-2-(N-methyl-N-methylsulfonylamino)pyrimidin-5-yl]-(3R)-3-hydroxy-5-oxo-(E)-6-heptenoate of formula (11) by using diethyl methoxy borane and sodium borohydride in presence of solvent, selected from the group consisting of tetrahydrofuran, methanol, ethanol, dichloromethane, dichloroethane and chloroform, at a temperature in the range of −75° C. to −82° C. for the period of 2 hours to 4 hours to obtain tertiary butyl 7-[4-(4-fluorophenyl)-6-isopropyl-2-(N-methyl-N-methylsulfonylamino)pyrimidin-5-yl]-(3R,5S)-dihydroxy-(E)-6-heptenoate of formula (12);

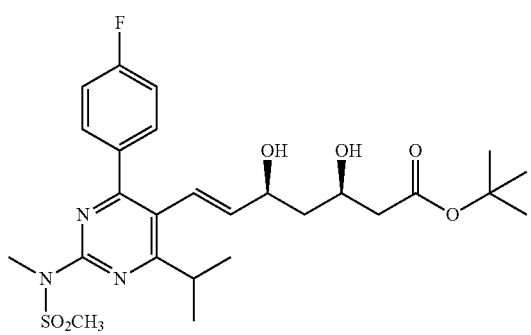

12

Step 11) converting the tertiary butyl 7-[4-(4-fluorophenyl)-6-isopropyl-2-(N-methyl-N-methylsulfonylamino)pyrimidin-5-yl]-(3R,5S)-dihydroxy-(E)-6-heptenoate of formula (12) by using aqueous sodium hydroxide in presence of solvent, selected from the group consisting of water, toluene, ethanol, dichloromethane, dichloroethane and chloroform, at a temperature in the range of 20° C. to 35° C. for the period of 2 hours to 4 hours to obtain 7-[4-(4-fluorophenyl)-6-isopropyl-2-(N-methyl-N-methylsulfonylamino)pyrimidin-5-yl]-(3R,5S)-dihydroxy-(E)-6-heptenoic acid sodium salt of formula (13);

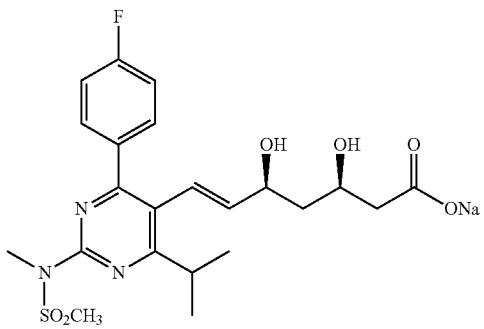

13

Step 12) converting the 7-[4-(4-fluorophenyl)-6-isopropyl-2-(N-methyl-N-methylsulfonylamino)pyrimidin-5-yl]-(3R,5S)-dihydroxy-(E)-6-heptenoic acid sodium salt of formula (13) by using water and calcium chloride at a temperature in the range of 15° C. to 30° C. for the period of 0.5 hour to 2 hours to obtain 7-[4-(4-fluorophenyl)-6-isopropyl-2-(N-methyl-N-methylsulfonylamino)pyrimidin-5-yl]-(3R,5S)-dihydroxy-(E)-6-heptenoic acid calcium salt of formula (I).

4. The process as claimed in claim 3, wherein said solvent in Step 1 is dichloromethane.

5. The process as claimed in claim 3, wherein said temperature in Step 1 is range of 20° C. to 25° C.

6. The process as claimed in claim 3, wherein said period in Step 1 is 20 hours.

7. The process as claimed in claim 3, wherein said solvent in Step 2 is methanol.

8. The process as claimed in claim 3, wherein said base in Step 2 is sodium hydroxide.

9. The process as claimed in claim 3, wherein said temperature in Step 2 is range of 10° C. to 15° C.

10. The process as claimed in claim 3, wherein said period in Step 2 is 3 hours.

11. The process as claimed in claim 3, wherein said solvent in Step 3 is t-butanol.

12. The process as claimed in claim 3, wherein said base in Step 3 is sodium hydroxide.

13. The process as claimed in claim 3, wherein said temperature in Step 3 is range of 25° C. to 35° C.

14. The process as claimed in claim 3, wherein said period in Step 3 is range of 3 hours to 4 hours.

15. The process as claimed in claim 3, wherein said solvent in Step 4 is ethanol.

16. The process as claimed in claim 3, wherein said base in Step 4 is sodium hydroxide.

17. The process as claimed in claim 3, wherein said temperature in Step 4 is range of 28° C. to 30° C.

18. The process as claimed in claim 3, wherein said period in Step 4 is 20 hours.

19. The process as claimed in claim 1, wherein the compound of formula (4) is further converted into Rosuvastatin calcium of formula (I).

20. The process as claimed in claim 2, wherein the compound of formula (5) is further converted into Rosuvastatin calcium of formula (I).

* * * * *